United States Patent [19]

Howe

[11] 3,968,035
[45] July 6, 1976

[54] SUPER-OXYGENATION METHOD

[75] Inventor: Robert H. L. Howe, West Lafayette, Ind.

[73] Assignee: Eli Lilly and Company, Indianapolis, Ind.

[22] Filed: Feb. 21, 1975

[21] Appl. No.: 551,863

Related U.S. Application Data

[63] Continuation of Ser. No. 348,377, April 5, 1973, abandoned.

[52] U.S. Cl. .............................. 210/15; 210/63 R; 426/7; 195/109
[51] Int. Cl.² .......................................... C12B 1/14
[58] Field of Search ............ 210/221, 208, 219, 14, 210/15, 220, 63, 205; 261/87, 120; 195/109, 142, 143; 426/7

[56] References Cited
UNITED STATES PATENTS

| 3,092,678 | 6/1963 | Braun | 210/15 |
| 3,625,834 | 12/1971 | Muller | 195/109 |
| 3,630,498 | 12/1971 | Bielinski | 210/219 |
| 3,752,742 | 8/1973 | Jaekel et al. | 210/15 |
| 3,775,307 | 11/1973 | McWhirter et al. | 210/14 |

Primary Examiner—Charles N. Hart
Assistant Examiner—Benoit Castel
Attorney, Agent, or Firm—Ralph W. Ernsberger; Everet F. Smith

[57] ABSTRACT

Super-oxygenation of bio-oxidizable fluid in a bio-oxidation reactor is accomplished by continuously transferring a stream of said fluid from the top of the column of fluid in said reactor to an oxidator vessel equipped with a high-shear agitator, introducing an oxygen containing gas into the bottom of the column of fluid in said vessel, rapidly revolving said agitator concurrently with the flow of said gas into said vessel, and continuously transferring a stream of said fluid from the top of the column of fluid in said vessel to the bottom of the column of fluid in said reactor.

12 Claims, 1 Drawing Figure

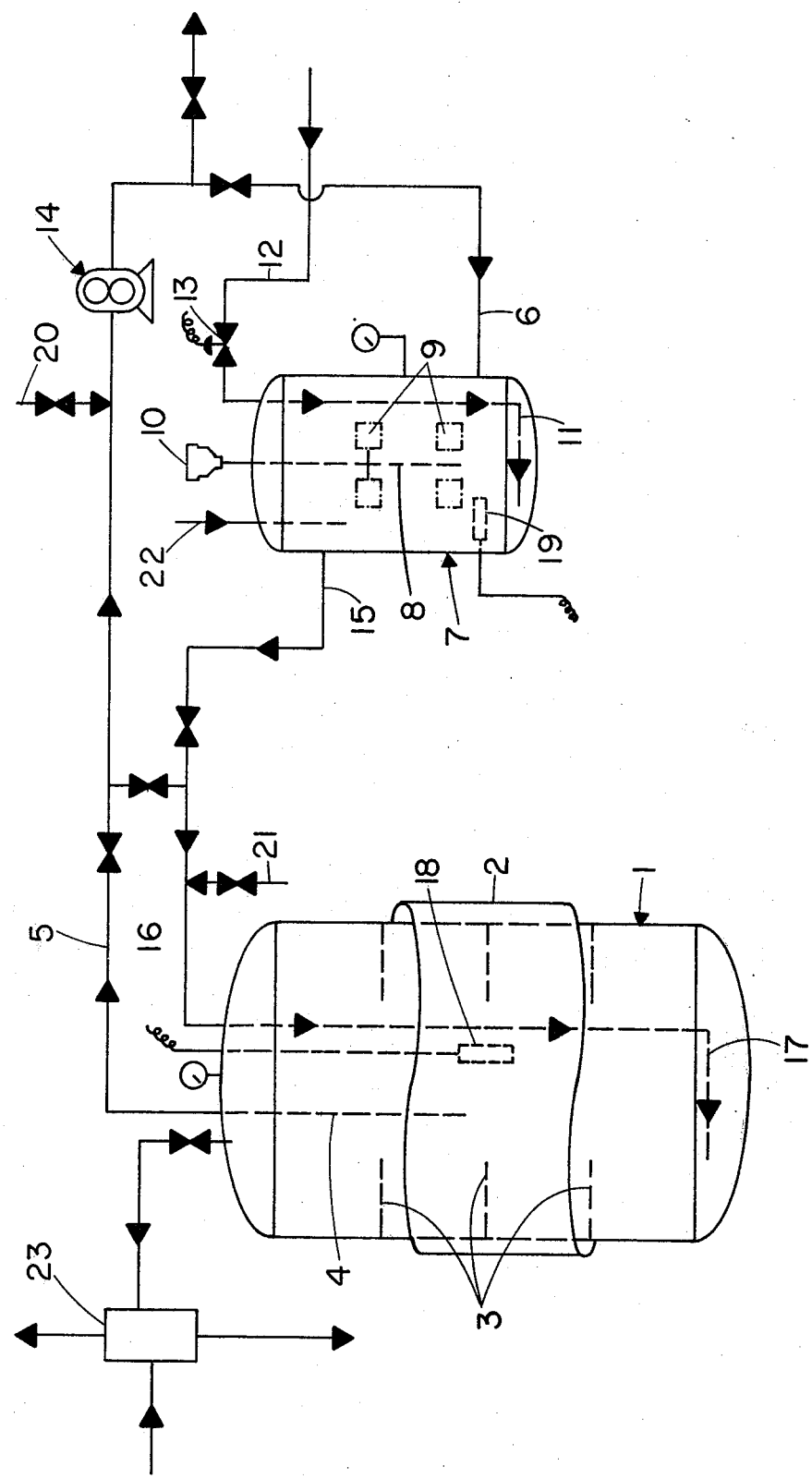

SUPER-OXYGENATION METHOD

CROSS-REFERENCE

This application is a continuation of co-pending application Ser. No. 348,377, filed Apr. 5, 1973 now abandoned.

BACKGROUND OF THE INVENTION

1. Field of Invention

This invention relates to a chemical engineering process. More particularly, this invention relates to a superoxygenation method that increases the dissolved oxygen in a bio-oxidizable fluid in a bio-oxidation reactor.

2. Prior Art

Long before it was understood, it was recognized that the waste products from living things were disposed of more readily in cascading water than stagnant pools. As an understanding developed that oxygen was required to degrade such waste, and it became known that a small amount of oxygen can be dissolved in water, efforts were directed toward the artificial aeration of water.

Early development of the trickling filter provided a means for adding oxygen to bio-oxidizable fluids, thus hastening the bio-oxidation process. Means for sparging air into such fluids below the surface thereof so that the upward movement of the gas through the liquid would result in some oxygen being dissolved therein came later and provided a more rapid bio-oxidation procedure.

When the need for stimulating the aerobic growth of microorganisms came as the discovery of antibiotics for treating disease burst upon the world in the thirties, the sparging of air into fermentation media in deep tank cultures permitted the large scale production of such useful things as penicillin. A large bank of technology has been built-up relating to the most efficient means for providing oxygen for the growth of the mycelia which produce antibiotics. Classically, large pumps are employed which compress air, push such compressed air through sterilizing filters, and out through spargers located near the bottom of columns of fermentation media into such media, all the while agitating the media to maintain as much homogenity as possible. Some of the oxygen in the air sparged into the fermentation media is dissolved in the liquid phase. This dissolved oxygen is utilized in the biological system that marks the growth and proliferation of the mycelia.

But even at its best, the sparging of compressed air into a bio-oxidizable fluid to provide dissolved oxygen for the life processes for the microorganisms that dispose of waste from living things, and produce the life saving antibiotics is an inefficient process. Less than 1 percent of the oxygen that is sparged into the bio-oxidizable fluid is ever dissolved therein, and large quantities of energy are required to pump the air through the spargers. This is at least partly due to the lower limit of the size of the air bubbles that can be effectively produced by conventional spargers.

Accordingly, it is an object of this invention to provide a super-oxygenation method that significantly increases the oxygen dissolved in a bio-oxidizable fluid over that effected from sparging a similar volume of oxygen into such fluid, a method useful for antibiotics production, food fermentation or biological waste treatment processes.

It is another object of this invention to provide a super-oxygenation method that significantly increases the total number of the bubbles from a unit volume of gas dispersed in a bio-oxidizable fluid over that effected from sparging a similar volume of gas into such fluid.

It is still another object of this invention to provide a super-oxygenation method that significantly increases the surface area of the bubbles from a unit volume of gas dispersed in a bio-oxidizable fluid over that effected from sparging a similar volume of gas into such fluid.

It is yet another object of this invention to provide a super-oxygenation method that requires significantly less energy to effectively dissolve a given quantity of oxygen in a bio-oxidizable fluid than that required by the conventional sparging method.

SUMMARY

It has now been discovered that the quantity of oxygen dissolved in a bio-oxidizable fluid in a bio-oxygenation reactor can be significantly increased over that which can be effected by conventional sparging methods by utilizing a novel super-oxygenation method comprising the steps of:

1. Continuously transferring a stream of said fluid from the top of the column thereof in said reactor to a small oxidator vessel.

2. Rotating a high-shear agitator in the bio-oxidizable fluid transferred to said oxidator vessel while an oxygen containing gas is being introduced under pressure into said fluid near the bottom of the column thereof. And, 3. Continuously transferring a stream of such oxygenated fluid from the top of the column thereof to the bottom of the column of bio-oxidizable fluid in said reactor. The bio-oxygenation reactor and the oxidator vessel are in a closed system, and may or may not be under pressure, and a pump is utilized to make the transfer. The oxygen can be from either vaporized liquid oxygen or compressed air.

BRIEF DESCRIPTION OF THE DRAWING

The accompanying drawing is a schematic diagram of the equipment involved in the super-oxygenation method and depicts a closed system in which the method is operated under pressure.

DESCRIPTION OF THE PREFERRED EMBODIMENTS

In the following detailed description of the embodiments of this invention, reference is made to the accompanying drawing.

The super-oxygenation method for increasing the oxygen dissolved in a bio-oxidizable fluid in a bio-oxidation reactor comprises:

1. Continuously transferring a stream of bio-oxidizable fluid from a bio-oxidation reactor to an oxidator vessel, said reactor and said vessel being connected in a closed system and transfer being effected by means of a pump (sterilizable as needed), said stream of bio-oxidizable fluid being transferred from the top of the column of said fluid in said reactor to the bottom of the column of bio-oxidizable fluid in said vessel.

2. Rotating a high-shear agitator in the column of bio-oxidizable fluid in said vessel while introducing an oxygen containing gas into said fluid at the bottom of said column. And, 3. Continuously transferring a stream of the oxygenated bio-oxidizable fluid from the top of the column thereof in said vessel to the bottom of the column of bio-oxidizable fluid in said reactor.

Referring to the drawing there is seen a bio-oxidation reactor 1. The reactor 1 is depicted with a longer vertical than horizontal axis. And this is the preferred configuration. But it is not necessary, as the horizontal axis can be longer than the vertical axis and satisfactory performance can still be obtained. When the horizontal axis is very much greater than the vertical axis a problem arises in evenly distributing the stream of oxygenated bio-oxidizable fluid from the oxidator vessel over the entire horizontal cross-section of the reactor. However, proper placement of the outlets for the oxygenated bio-oxidizable fluid can effectively provide a relatively even distribution of the returning highly oxygenated fluid.

The capacity of the reactor 1 can be varied over a wide range. Reactors of as little as a few hundred gallons can be successfully utilized for the fermentation of antibiotics, while reactors useful for waste treatment can be of a million or more gallons capacity. Generally, antibiotics are fermented in reactors of up to about 60 thousand gallons capacity and waste treatment reactors range up to a quarter million gallon capacity.

It is useful to provide a configuration that makes it easy to minimize the energy requirements for maintaining a homogenous mixing. In the production of antibiotics, the presence of suspended solids requires the use of a mixer to keep the solids uniformly distributed throughout the column of fluid. But other applications of the super-oxygenation method of this invention, such as the bio-oxidation of fluid wastes may require no more than the agitation produced as the ultra small bubbles of gas rise to the top of the column of fluid in the reactor. Mixing is also further accomplished by the rapid intermingling of the liquid in the bio-oxidation reactor with the stream of oxygenated fluid from the oxidator.

The reactor can be enrobed in a jacket 2, shown cut-away in the drawing. A jacket is useful on the reactor when it is necessary to control the temperature therein. For example, in the fermentation of antibiotics it is usually desirable to maintain a constant temperature in the reactor, and this temperature is generally higher than normal room temperature. While highly exothermic bio-oxidation processes are not encountered frequently, a jacket 2 provides a means for removing heat from such processes.

It is generally desirable to provide baffles in a bio-oxidation reactor to aid in maintaining homogenity of the reaction medium. Horizontal baffles 3 are shown in the accompanying drawing. Vertical baffles (not shown) can also be utilized. Or, both horizontal and vertical baffles can be employed simultaneously, or a reactor with no baffles at all can be successfully operated.

The oxidator vessel 7 is depicted in the drawing as having a longer vertical than horizontal axis, and such is the preferred configuration in the novel process of this invention. A vessel 7 having a diameter to height ratio of from about 1:2 to 1:10 can serve as a satisfactory oxygenator. As the height comes closer to equaling the diameter, the energy needed to operate the high-shear agitator 8 increases over that necessary to successfully provide the high-shear agitation and the costs of operation go up accordingly. It has been found that a highly efficient high-shear agitator 8 has impeller blades 9 that have a diameter of about 50 percent of the inside diameter of vessel 7. Moreover, the number of impellers 9 will vary with the height of the tank, but it has been found that there should be a minimum of two impellers 9 with blades at either 90°, 120° or 180°. More than four blades on each impeller contributes little to the oxygenation and are not recommended. The preferred configuration has three vertical blades, each at 120° from the other.

A means 10 is required to rotate the high-shear agitator 8 and provision must be made for varying the speed of the high-shear agitator. Agitator speeds from 150 to 1800 rpm are useful and the effectiveness of the oxygenation will be effected by the number of impellers, the area of the blades and the ratio of the diameter of the impellers 9 to the diameter of the vessel 7. Preferably, when the latter ratio is 1 to 2, the number of impellers is 2 and the area of the blades approximates the cross-sectional area of the vessel 7.

The volume of the oxidator vessel 7 is always considerably less than the volume of the bio-oxidation reactor 1, and is scaled to conform to the capacity of the latter. In an antibiotic fermentation process, the bio-oxidation reactor 1 should have a volume of from 10 to 30 or more times the volume of the oxidator vessel 7, preferably about 20 times. In waste treatment processes the relation of the volumes will usually be from 1 to 50 to 1 to 200, with a ratio of about 1 to 100 preferred.

The bio-oxidation reactor 1 and the oxidator vessel 7 are operated in a closed system. Pump 14 is employed to draw a continuous stream of bio-oxidizable fluid from the inlet pipe 4, in reactor 1 through transfer line 5 to the pump and into vessel 7 through discharge line 6. The oxygenated bio-oxidizable fluid leaves vessel 7 through outlet 15, travels in a continuous stream through transfer line 16 and is returned to reactor 1 through discharge line 17. Oxygen, in the form of either vaporized liquid oxygen or compressed air is conveyed to motor valve 13 through supply line 12. Motor valve 13 controls the flow of oxygen into vessel 7. Oxygen is introduced into vessel 7 through discharge line 11.

The oxygen concentration in vessel 7 is measured by dissolved oxygen probe 19, and in reactor 1 by dissolved oxygen probe 18. The measurements recorded from probes 17 and 18 are integrated and motor valve 13, controlling the flow of oxygen into vessel 7 is actuated from such integration and varies the oxygen volume to meet the demands of the system.

The entry of various materials into the system can be effected through entry ports 20, 21 and 22. Entry port 20 is generally utilized to add make-up fluid to the system, while entry port 21 is a convenient place to introduce steam for sterilization of the system where such is required. Anti-foam material can be added through entry port 22 when such is needed. Distribution box 23 is employed as the exhaust port for the excess gas leaving the upper surface of the bio-oxidizable fluid in reactor 1. Generally a low back pressure is maintained on the system by regulating the exhaust of the gas through the distribution box 23. Entrained fluid is also removed here and directed to an appropriate disposal. When such is required, the exhaust gas from the distribution box 23 can be conveyed to an incinerator to remove objectional odors before release to the atmosphere. Alternatively, the process can be operated with the top of the column of fluid in the bio-oxidation reactor 1 open to the atmosphere, such as in a waste treatment process where the odors are of no consequence.

The equipment employed in the useful process of this invention having been described hereinbefore, the actual operating parameters are detailed hereinafter.

The novel method of this invention is operated by adding a bio-oxidizable fluid, such as an antibiotic fermentation media through entry port 20 and sterilizable pump 14 to oxidator vessel 7. The addition to vessel 7 is made near the bottom thereof at inlet 6. The vessel 7 is filled to the level of outlet 15 near the top of said vessel 7, whereupon the bio-oxidizable fluid moves through transfer line 16 to the discharge outlet 17 near the bottom of reactor 1. The addition of the bio-oxidizable fluid is continued until the desired amount is present in reactor 1. Under all circumstances it is necessary that the level of the fluid in reactor 1 is higher than the transfer outlet 4 in the upper section of said reactor 1. With reactor 1 and vessel 7 charged with the appropriate quantity of bio-oxidizable fluid, the high-shear agitator 8 is actuated and revolved at the rpm that is the equivalent of pulling from about 5 to about 15 hp per 1000 gallons of fluid in said vessel 7. Preferably the agitator should pull about 10 hp to achieve satisfactory super-oxygenation of said bio-oxidizable fluid. When this amount of energy is consumed, agitator 8 will normally be turning at from about 150 to about 1800 rmp, depending on the design of vessel 7 and the impellers 9 on said agitator 8.

With the high-shear agitator 8 turning, pump 14 is actuated and adjusted to transfer bio-oxidizable fluid from the bottom of reactor 1 to vessel 7 at a rate that will provide a renewal of the fluid in vessel 7 every 30 to 240 seconds. Preferably, the volume of fluid being transferred from reactor 1 to vessel 7 and back to vessel 1 should be at a rate equal to the capacity of vessel 7 being transferred every 90 to 120 seconds.

The introduction of the oxygen containing gas through discharge outlet 11 in vessel 7 is begun after the agitator has been set to revolve at the desired rate and the continuous transfer of the bio-oxidizable fluid has been established at an appropriate rate.

The oxygen containing gas is introduced into said fluid in vessel 7 at a pressure of from about 1 to about 40 psig at the discharge outlet 11.

The quantity of oxygen introduced into vessel 7 is metered to provide from about 200 to about 250 pounds of oxygen, as oxygen, whether vaporized from liquid oxygen or contained in compressed air, per 1000 gallons of bio-oxidizable fluid contained in vessel 7 per hour, per 10 hp energy consumed in the high-shear agitation.

Probes 19 and 18 measure the amount of dissolved oxygen in vessel 7 and reactor 1, respectfully. These measurements are integrated and used to control the rate of oxygen addition to vessel 7. In an antibiotic fermentation process a point is eventually reached where the biological oxygen demand nears zero as the biological system is self-limiting. At a pre-determined point the bio-oxidation reaction can be terminated. The system is drained, cleaned, sterilized and a new cycle begun. A waste treatment process, wherein oxygen is required to keep the microbes going that effect the biological conversion, also has a biological oxygen demand and is self-limiting. Oxygen can be provided for the aerobic microbes and when there is no longer food (waste) on which the microbes can feed there is no need for oxygen, the measurements of the dissolved oxygen predict this condition and the further addition of oxygen is stopped, the system emptied, a new charge made and the cycle repeated.

The essence of the super-oxygenation method of this invention is the employment of high-shear agitation in a portion of the total of the bio-oxidizable fluid in a bio-oxidization reaction system concomittantly with the introduction of an oxygen containing gas, such as vaporized $O_2$ from liquid oxygen or compressed air, into such portion wherein the gas is reduced to minutely fine bubbles of the order of from about $10^{-1}$ centimeter to about $10^{-4}$ centimeters in diameter. These very fine bubbles offer a far greater surface area at the gas-liquid interface than is effected by conventional sparging methods. Bubbles generated by ordinary sparging are generally of the neighborhood of about 5.0 mm. in diameter or greater. When 1 ml. of gas is dispersed to a diameter of 5.0 mm., about 15 bubbles are formed having a surface area of about 19 square centimeters. However, when 1 ml. of gas is dispersed into bubbles of 1 mm diameter, ($10^{-1}$ centimeters) there are $1.9 \times 10^3$ bubbles formed having a surface area of about 60 square centimeters. And when the bubbles are $10^{-4}$ centimeters in diameter, 1 ml. of gas will form $1.9 \times 10^{12}$ bubbles having a surface area of $6 \times 10^4$ square centimeters.

The production of antibiotics necessarily is accompanied by a substantial quantity of suspended solids in the bio-oxidizable fluid. These solids are the growing mycelia. This fact, plus the large capacity tanks employed in such fermentation processes, make the energy requirements astronomical to operate a high-shear agitator directly in the bio-oxidation reactor itself. Moreover, there is no useful purpose served by super-oxygenating the bio-oxidizable fluid in the fermenters as the 1500 to 2000 ppm of dissolved oxygen which can be achieved in an oxidator vessel cannot be utilized efficiently and there would be a costly waste.

Additionally, the novel method of this invention can be adopted as a means for augmenting the oxygen dissolved in bio-oxidation fluids by conventional sparging methods. And either relatively pure $O_2$ from vaporized liquid oxygen or compressed air can be employed as the source of the oxygen. When this process is used to augment the oxygen provided by the conventional sparging method, an intermittent operation can be programmed into system, and with instrumentation known to those skilled in the art, additive dissolved oxygen supplied on demand.

As with antibiotic fermentations, super-oxygenation of waste-treatment fluids in large tanks holding a hundred-thousand gallons or more would require prodigious quantities of energy, and again no particular advantage would be realized as the microbes can only consume oxygen at a fixed rate and the providing of dissolved oxygen beyond reasonable amounts is a costly waste.

The problem has been to achieve a greater amount of dissolved oxygen. Large bubbles do not make this an easy task, as it is the total surface area of gas bubbles which influences the amount of dissolved oxygen in the bio-oxidizable fluid.

Conventional methods of sparging oxygen into an antibiotic fermenter results in a dissolved oxygen concentration of about 7 ppm maximum when the fermenter is operated at about 37°C. The useful method of this invention can increase the dissolved oxygen concentration significantly as shown in EXAMPLE 1.

EXAMPLE 1

An oxidator vessel 6 inches in diameter and 23 inches high was equipped with a high-shear agitator. The vessel had an effective capacity of 2.85 gallons. The vessel was connected in a closed system with a bio-oxidation reactor having an effective capacity of 445 gallons. The system was filled with water at room temperature. The high-shear agitator was run at 154 rpm and pulled 1.0 hp. The recycling pump was operated at a transfer rate of 1 gallon per minute. This meant that the fluid in the oxidator vessel was renewed every 170 seconds. Oxygen from a supply cylinder was introduced into the oxidator vessel at the rate of 0.018 pound per minute at 4.6 psig. After running for 5 minutes, the dissolved oxygen in the bio-oxidation reactor was measured as 9.9 ppm average. The calculated dissolved oxygen, based on the rate and time of the oxygen feed, was 14.0 ppm maximum. The apparent dissolved oxygen in the oxygenator vessel was calculated, based on the 9.9 ppm in the reactor, at 1,560 ppm. The operation showed a 70 percent efficiency in converting gaseous oxygen into dissolved oxygen in a bio-oxidation reactor. The 9.9 ppm of dissolved oxygen in the bio-oxidation reaction was significantly greater than the 7.0 ppm maximum which can be achieved with sparged gas.

Moreover, in waste treatment processes, employment of the useful method of this invention results in substantial economies in the operation. Tests showed that when compressed air at from 5 to 10 psig at the discharge outlet in the oxidator was utilized as the source of the oxygen, about 25 pounds of oxygen was dissolved per KWH consumed in energy in compressing the air. On the other hand, at the maximum only about 3 pounds of oxygen can be dissolved per KWH consumed in energy in compressing the air to 5 to 10 pounds when conventional sparging methods are employed. This indicated energy savings is offset by the added energy required to operate the high-shear agitator and the transfer pump. Experiments showed that when pure oxygen was used as the source of the oxygen, about 25 pounds or more of oxygen at 1 atmosphere were dissolved per KWH of energy consumed by the agitator. As compressed air is about one-fifth oxygen, about 5 KWH of energy is needed to dissolve 25 pounds of oxygen from such a source. Furthermore, at a dissolved oxygen content of 300 ppm, the transfer of 10,000 gallons of bio-oxidizable fluid to the oxygenator is required for every 25 pounds of dissolved oxygen effected. Engineering calculations show that about 0.5 KWH of energy is required to transfer the 10,000 gallons of bio-oxidizable fluid from a bio-oxidation reactor to an oxygenator vessel and return.

Summing the energy requirements of the super-oxygenation method of this invention it was determined that a total of 6.5 KWH of energy is consumed in effecting the dissolution of 25 pounds of oxygen from compressed air. This compares with the most favorable energy requirement of the conventional sparging method of 8.3 KWH of energy consumed per 25 pounds of oxygen dissolved from compressed air. An advantage of 1.8 KWH minimum in favor of the useful method of this invention. A reduction of better than 20 percent in the energy requirements to provide the oxygen needed to support the aerobic microorganisms which turn bio-degradable waste into bio-oxidized waste.

The useful method of this invention can also be adapted to the fermentation process of foods and beverages requiring oxygenation with a similar economic benefit in lowered energy requirements to achieve a comparable level of dissolved oxygen in fermentation media.

What is claimed is:

1. A method for continuously super-oxygenating a portion of the bio-oxidizable fluid from a bio-oxidation reactor to increase the concentration of oxygen dissolved in such fluid and reduce the energy required to effect the dissolution of such oxygen in such fluid comprising the steps of:
   a. continuously transferring a stream of said fluid in said reactor from a point near the top of the column of said fluid to a point near the bottom of an oxidator vessel equipped with a high shear agitator, said vessel having a capacity of from about one-tenth to one-two hundreth of the capacity of said reactor and having a diameter to height ratio of from about 1:2 to about 1:10 and said agitator having a diameter of from about 1:3 to 2:3 of the diameter of said vessel and impellers thereon having an effective surface area about the same as the cross-sectional area of said vessel, said reactor and said vessel being connected in a closed system;
   b. filling said vessel with a column of said fluid from said reactor to a point near the top of said vessel where there is disposed a return conduit from said vessel to a point near the bottom of said vessel to a point near the bottom of said reactor;
   c. introducing an oxygen containing gas into said fluid in said vessel at a point near the bottom of said vessel, at a pressure of from about 1.0 to about 40 psig;
   d. revolving said agitator in said fluid in said vessel while said gas is being introduced thereinto;
   e. operating said agitator at from about 150 to about 1,800 rpm wherein the energy utilization is from about 5 to about 15 horsepower per 1,000 gallons of said fluid in said vessel;
   f. shearing said oxygen containing gas into submillimeter bubbles of the order of from about $10^{-1}$ to about $10^{-4}$ centimeters in said fluid; and
   g. continuously transferring a stream of the bio-oxidizable fluid containing the sub-millimeter bubbles of oxygen containing gas from said vessel to a point near the bottom of said reactor, said stream being taken from a point near the top of said column of said fluid in said vessel, said transferring being conducted at a rate such that the volume of said fluid in said vessel is renewed every 30 to 240 seconds.

2. The method according to claim 1 wherein a pump is utilized to continuously transfer said fluid from said reactor to said vessel and return.

3. The method according to claim 1 wherein the ratio of the diameter of said agitator to the diameter of said vessel is about 1:2.

4. The method according to claim 1 wherein said oxygen containing gas is substantially pure $O_2$ from vaporized liquid oxygen.

5. The method according to claim 1 wherein said oxygen containing gas is compressed air.

6. The method according to claim 1 wherein the transfer rate of said fluid is such that the volume of said fluid in said vessel is renewed every 90 to 120 seconds.

7. The method of super-oxygenating the growth medium of an antibiotic fermentation process comprising super-oxygenating such medium according to claim 1.

8. The method of super-oxygenating a food fermentation process requiring oxygenation comprising super-oxygenating said process according to claim 1.

9. The method of super-oxygenating a beverage fermentation process requiring oxygenation comprising super-oxygenating said process according to claim 1.

10. The method of super-oxygenating the bio-degradable matter in a waste treatment process comprising super-oxygenating said process according to claim 1.

11. The method of claim 10 wherein said bio-degradable matter is comprised of waste from an antibiotic fermentation process.

12. The method of claim 10 wherein said bio-degradable matter is comprised of liquid organic waste entering a sewage disposal process.

* * * * *